United States Patent
Ahn et al.

(10) Patent No.: US 6,566,567 B2
(45) Date of Patent: May 20, 2003

(54) CATALYST AND METHOD FOR PRODUCING 1,1-DIFLUOROETHANE

(75) Inventors: Byoung Sung Ahn, Seoul (KR); Jung Hwan Song, Seoul (KR); Dong Ju Moon, Seoul (KR); Kun You Park, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/897,899

(22) Filed: Jul. 5, 2001

(65) Prior Publication Data

US 2002/0107421 A1 Aug. 8, 2002

(30) Foreign Application Priority Data

Dec. 8, 2000 (KR) .......................................... 00-74615

(51) Int. Cl.⁷ ............................ C07C 17/10; B01J 27/13
(52) U.S. Cl. ...................................... 570/176; 502/230
(58) Field of Search ........................... 570/176; 502/230

(56) References Cited

U.S. PATENT DOCUMENTS 5,136,113 A    8/1992    Rao

FOREIGN PATENT DOCUMENTS

JP    3-83 940     4/1991
JP    7-126 197    5/1995

OTHER PUBLICATIONS

A. Wiersman et al., Catalysis Today 27, (1996), pp. 257–264.

P. Albers et al., Journal of Catalysis 181, (1999), pp. 145–154.

*Primary Examiner*—Alan Siegel
(74) *Attorney, Agent, or Firm*—Finnegan, Henderson, Farabow, Garrett & Dunner, L.L.P.

(57) ABSTRACT

The present invention relates to a catalyst for producing 1,1-difluoroethane (HCFC-152a) and producing method thereof. More particularly, it is to provide the catalyst prepared by impregnating palladium on the active carbon pretreated with an aqueous hydrogen fluoride solution and an aqueous hydrogen chloride solution in series and its use in the production of 1,1-difluoroethane (HCFC-142b) by dehydrochlorinating 1,1-difluoro-1-chloroethane at 240–300° C. in the supplying molar ratio of 2–6 ($H_2$/HCFC-142b) with maximizing a selectivity toward the product of HCFC-152a.

5 Claims, No Drawings

CATALYST AND METHOD FOR PRODUCING 1,1-DIFLUOROETHANE

BACKGROUND OF THE INVENTION

Field of the Invention

The present invention relates to a catalyst for producing 1,1-difluoroethane ($CHF_2CH_3$, hereinafter referred to as the "HCFC-152a") and producing method thereof. More particularly, it is to provide the catalyst prepared by impregnating palladium on the active carbon pretreated with an aqueous hydrogen fluoride solution and an aqueous hydrogen chloride solution in series and its use in the production of 1,1-difluoroethane by dehydrochlorinating 1,1-difluoro-1-chloroethane ($CF_2ClCH_3$, hereinafter referred to as the "HCFC-142b") at 240–300° C. in the supplying ratio of 2–6 ($H_2$/HCFC-142b) with maximizing a selectivity toward the product of HCFC-152a.

Chlorofluorocarbons (hereinafter referred to as the "CFCs") were widely used for refrigerants, foaming agents, cleaning solvents, and aerosol propellants due to its non-toxicity and stabilities against chemicals and heat However, since it has been reported that CFCs are released into stratospheric layer and their chlorine atoms decomposed by UV light destroy the earth's ozone layer, the current concern over the use of CFCs and their effect on the environment has been emphasized. According to memorandum of Montreal, the developed countries have prohibited producing CFCs and imports and exports since 1996 and the developing countries also reduce the use of CFCs up to 50% by 2005 and will be disused by 2010. There has been an increasing demand for producing hydrochlorofluorocarbons (hereinafter referred to as the "HCFCs") by replacing chlorine atoms by hydrogen or fluorine atoms as alternatives for CFCs used as refrigerants, foaming agents and the like. However, even if HCFCs are decomposed faster than CFCs, they are still environmental hazard materials because they also contain chlorine atoms in the molecules.

On the other hand, the development for manufacturing processes of hydrofluorocarbons (hereinafter referred to as "HFCs") as excellent alternatives for CFCs has been rapidly increased due to its advantages in no harming earth's environment and ozone layer.

Of manufacturing processes, hydrogenolysis of CFCs provides HFCs and especially hydrogenolysis in the presence of a catalyst is proved as a very useful method for producing HFCs. Examples for producing HFCs from CFCs or HCFCs are HFC-125($CF_3CF_2H$) from CFC-115 ($CF_3CF_2Cl$), HFC-32($CH_2F_2$) from CFC-12($CF_2Cl_2$), and HFC-152a($CHF_2CH_3$) from HCFC-142b($CF_2ClCH_3$).

Japan Patent No. 3-83940 discloses a method for producing HFC-152a by hydrogenolysis of CFC-142b at 300–340° C. in the presence of a catalyst prepared by impregnating a metal (platinum, palladium, rhodium, nickel, or a mixture thereof) on an active carbon. The yield of the reaction is reported as 80% but its reactivity and selectivity are not mentioned. And the lifetime of the catalyst which is one of the most important matters in hydrogenolysis of halogen-containing compounds has not been mentioned, either. In general, if the temperature for hydrogenolysis is higher than 300° C., sintering of a metal catalyst can occur and its activity rapidly decreases and this is proved in the comparison examples disclosed in Japan Patent No. 7-126197. Thus, in order to solve these problems Japan Patent No. 7-126197 discloses an addition of bismuth on the palladium catalyst to enhance the activity and selectivity. In the hydrogenation of HCFC-142b with hydrogen (molar ratio of hydrogen:HCFC-142b=4:1) performed at over 300° C. in the presence of palladium and bismuth, a reactivity of HCFC-142b was 80% and a selectivity toward HFC-152b was 86%, while the activity was reduced to 30% in the absence of bismuth after 10 hrs of reaction. However, the reaction temperature is relatively high over 300° C. and it produces $C_2H_5F$ over 10% as a by-product.

There have been attempts to prepare improved methods for preparing palladium catalyst (Pd/C) such as pretreatment of an active carbon or addition of platinum type metal to palladium. Pretreatments of an active carbon with acid or alkali in the hydrogenation of CFC and HCFC are disclosed in U.S. Pat. No. 5,136,113, Wiersma (A. Wiersma, E. J. A. X. van de Sandt, M. Makkee, H. van Bekkum, and J. A. Moulijn, Catal. Today, 27, (1996) 257), and Albers (P. Albers, R. Burmeister, K. Seibold, G. Prescher, S. F. Parker, and D. K. Ross, J. Catal. 181, (1999) 145). It can be expected that the pretreatment of an active carbon can reduce impurities within the active carbon and enhance distribution of a metal catalyst and thus, improve its activity. However, experiments are essentially required to find better pretreatment method and preparation method of a catalyst and to maximize reaction conditions.

SUMMARY OF THE INVENTION

Palladium supported on an active carbon (Pd/C) is widely used commercial catalyst for hydrogenation. However, if the reaction temperature is low in the hydrogenation of CFC and HCFC, the reactivity becomes poor and if it is high, an activity rapidly decreases due to sintering of palladium catalyst. It is required to obtain the preparing method of a catalyst and appropriate reaction conditions because sintering can be affected by used support, preparing method and reaction temperature. And further, it is essentially required to enhance the selectivity toward dechlorination in dehalogenations of dechlorination and defluorination.

As a result of that inventors of the present invention have investigated various pretreatment methods of active carbon as the support of palladium catalyst (Pd/C) used in the dehydrochloriation of HCFC-142b, the inventors have realized that the pretreatment of an active carbon with two acids sequentially affects the activity and selectivity of the catalyst. In the present invention the catalyst prepared by impregnating palladium on the pretreated active carbon with hydrogen fluoride solution and hydrogen chloride solution in series is used in the dehydrochlorination reaction of HCFC-142b to HFC-152a.

DETAILED DESCRIPTION OF THE INVENTION

The present invention is characterized by a catalyst prepared by impregnating palladium on the active carbon pretreated with hydrogen fluoride solution and hydrogen chloride solution sequentially and a producing method of 1,1-difluoroethane by dehydrochlorination of 1,1-difluoro-1-chloroethane in the presence of said catalyst.

The present invention is described in detail as set forth hereunder.

The present invention is characterized by the catalyst prepared by impregnating palladium on the active carbon pretreated with hydrogen fluoride solution and hydrogen chloride solution sequentially. That is, the active carbon is treated with hydrogen fluoride solution in an appropriate concentration, washed, and retreated with hydrogen chloride solution.

In the process of pretreatment of the active carbon, both hydrogen fluoride solution and hydrogen chloride solution are used in the concentration of 0.1–2 mol/l. The mixture is stirred for more than 5 hrs, washed with distilled water till pH reaches to 4–7, preferably 6, and dried. Palladium chloride ($PdCl_2$) as a precursor of palladium (Pd) is dissolved in aqueous hydrogen chloride solution and then impregnated on the dried active carbon. The impregnated catalyst is dried at 50–200° C. and calcinated at 300–500° C. under atmospheric conditions to obtain the desired palladium catalyst.

The palladium catalyst (Pd/C) is used in hydrogenolysis of HCHC-142b and optimal reaction conditions such as temperature and molar ratio of reactants are investigated.

Hereunder is given a more detailed description of the present invention. However it should not be construed as limiting the scope of the present invention.

Comparative Example 1

Pretreatment of Active Carbon with Alkali (NaOH) and Acid (HCl)

Norit RB-1 active carbon (Norit) was treated with NaOH and HCl. Active carbon of 10 g was added to 2 l of 0.5 mol of aqueous NaOH solution and stirred for 8 hrs at room temperature. The active carbon was filtered out and washed with 4 l of distilled water till pH reached to below 8. And then it was treated with 2 l of 0.5 mol of aqueous HCl solution and stirred for 8 hrs at room temperature. The active carbon was filtered out, washed with 4 l of distilled water till pH reached to above 5, and dried at 100° C. for 24 hrs to give a support (hereinafter referred to as "AC—NaOH—HCl").

Comparative Example 2

Pretreatment of Active Carbon with Two Acids (HCl and Then HF)

Norit RB-1 active carbon (Norit) was treated with HCl and HF sequentially. Active carbon of 100 g was added to 2 l of 1 mol of aqueous HCl solution and stirred for 20 hrs at room temperature. The active carbon was filtered out and washed with distilled water till pH reached to above 5. And then it was treated with 2 l of 1 mol of aqueous HF solution and stirred for 20 hrs at room temperature. The active carbon was filtered out, washed with distilled water till pH reached to above 5, and dried at 100° C. for 24 hrs to give a support (hereinafter referred to as "AC—HCl—HF").

EXAMPLE 1

Pretreatment of Active Carbon with Two Acids (HF and Then HCl)

Norit RB-1 active carbon (Norit) was treated with HF and HCl sequentially. Active carbon of 100 g was added to 2 l of 1 mol of aqueous HF solution and stirred for 20 hrs at room temperature. The active carbon was filtered out and washed with distilled water till pH reached to above 5. And then it was treated with 2 l of 1 mol of aqueous HCl solution and stirred for 20 hrs at room temperature. The active carbon was filtered out, washed with distilled water till pH reached to above 5, and dried at 100° C. for 24 hrs to give a support (hereinafter referred to as "AC—HF—HCl").

EXAMPLE 2

Pretreatment of Active Carbon with Alkali and Two Acids (NaOH, HF and HCl Sequentially)

Surface characteristic of the active carbon was tried to be changed by treating with alkali before the treatment with two acids of Example 1 to improve activity and selectivity of the catalyst.

After Norit RB-1 active carbon (Norit) was treated with aqueous NaOH solution, the active carbon was further treated by the same procedure of Example 1. Active carbon of 10 g was added to 2 l of 0.5 mol of aqueous NaOH solution and stirred for 12 hrs at room temperature. The active carbon was filtered out and washed with distilled water till pH reached to below 8. And then it was treated by the same procedure of Example 1 to give a support (hereinafter referred to as "AC—NaOH—HF—HCl").

Catalysts were prepared with and without the pretreatment of the active carbon, so as prepared in Examples and Comparative Examples, by the following method.

Comparative Preparation 1

Preparation of Pd/AC Catalyst

Palladium was impregnated on Norit RB-1 active carbon (Norit) which was not pretreated to give Pd/AC. $PdCl_2$ of 0.3366 g was added to 43 ml of 0.087 mol HCl and the mixture was stirred to give clear solution at room temperature. The clear palladium solution was impregnated on 20 g of Norit RB-1 active carbon (Norit) which was not pretreated and dried at 100° C. for 12 hrs. And then first-impregnated catalyst was impregnated again and dried at 100° C. for 24 hrs. The dried catalyst was calcinated at 350° C. for 24 hrs to give 1 wt. % of Pd/AC.

Comparative Preparation 2

Preparation of Pd/AC—NaOH—HCl Catalyst

Palladium was impregnated on the AC—NaOH—HCl support prepared in Comparative Example 1, according to the procedure of Comparative Preparation 1 to give 1 wt. % of Pd/AC—NaOH—HCl.

Comparative Preparation 3

Preparation of Pd/AC—HCl—HF Catalyst

Palladium was impregnated on the AC—HCl—HF support prepared in Comparative Example 2, according to the procedure of Comparative Preparation 1 to give 1 wt. % of Pd/AC—HCl—HF.

Preparation 1

Preparation of Pd/AC—HF—HCl Catalyst

Palladium was impregnated on the AC—HF—HCl support prepared in Example 1, according to the procedure of Comparative Preparation 1 to give 1 wt. % of Pd/AC—HF—HCl.

Preparation 2

Preparation of Pd/AC—NaOH—HF—HCl Catalyst

Palladium was impregnated on the AC—NaOH—HF—HCl support prepared in Example 2, according to the procedure of Comparative Preparation 1 to give 1 wt. % of Pd/AC—NaOH—HF—HCl.

The elementary analysis and the nitrogen physisorption results of the prepared catalysts with carbon pretreatment conditions were summarized in tables 1 and 2, respectively. Not only the pretreatment of NaOH, HCl and HF solutions removed much amount of impurities from the active carbon but also its order affected size and distribution of palladium crystal during impreganation by changing surface characteristics. The influences of impurities contained in the catalysts on the activities and characteristics of the catalysts were elucidated by means of specific surface area [Autosorb-1, Quantachrome Corporation], elementary analysis [ICP, AASI], XRD (X-ray diffractometer) [Shimadzu, XRD-6000, Lab-X], and TEM (Transmission Electron Microscope) [CM30, Phillips, US].

The prepared catalyst with or without pretreatment of the active carbon was analyzed by elementary analysis and summarized in Table 1. The catalysts pretreated with HF—HCl and NaOH—HF—HCl were proved to contain much less impurities than those pretreated with other orders. Even though the catalysts were pretreated with the same acids (HF and HCl), amount of impurities contained therein was different with different order of treatment. However, chemical characteristic changes of the surface could not be identified by elementary analysis, XRD and IR analysis.

Specific surface area and average pore size were summarized in Table 2.

The prepared catalysts with pretreatment of alkali and acid or two acids showed improved characteristics compared to the prepared catalyst without pretreatment. One of the reasons for improved activity is due to the pretreatment of the activated carbon that allows the removal of impurities. Especially, the prepared catalyst with pretreatment of HF and HCl in series was proved to show improved specific surface area. Therefore, the order of acid treatment affects characteristics of the support and catalyst.

TABLE 1

Elementary Analysis of the Catalysts

| Category | Elementary analysis of impurities (wt. %) | | | | |
|---|---|---|---|---|---|
| | Fe | Mg | Ca | Si | Cl |
| Norit RB-1 prepared without pretreatment | 0.094 | 0.34 | 0.36 | 0.35 | Below 0.005 |
| Com. Prep. 1 | 0.094 | 0.34 | 0.36 | 0.35 | 0.59 |
| Com. Prep. 2 | 0.041 | 0.075 | 0.055 | 0.31 | 10.5 |
| Com. Prep. 3 | 0.022 | 0.052 | 0.030 | 0.18 | 6.79 |
| Prep. 1 | 0.025 | 0.045 | 0.035 | 0.037 | 13.8 |
| Prep. 2 | 0.027 | 0.044 | 0.029 | 0.040 | 12.9 |

TABLE 2

Pretreatment condition and Specific Surface Area and Average Pore Size of the Catalyst

| Catagory | Pretreatment | | Active carbon or Catalyst code | Specific surface area (m²/g) | Average pore size (Å) |
|---|---|---|---|---|---|
| | Alkali | Acid | | | |
| — | — | — | AC (Norit RB-1) | 658.8 | 10.37 |
| Com. Prep. 1 | — | — | Pd/AC | 767.8 | 9.78 |
| Com. Prep. 2 | NaOH | HCl | Pd/AC-NaOH-HCl | 774.1 | 10.39 |
| Com. Prep. 3 | — | HCl-HF | Pd/AC-HCl-HF | 802.4 | 10.25 |
| Prep. 1 | — | HF-HCl | Pd/AC-HF-HCl | 888.3 | 10.19 |
| Prep. 2 | NaOH | HF-HCl | Pd/AC-NaOH-HF-HCl | 875.6 | 10.30 |

Degree of Pd dispersion of the above-prepared catalysts was measured by TEM. The catalyst prepared without pretreatment of the active carbon showed aggregation of Pd. Degree of dispersion of the catalysts prepared with pretreatment of alkali and acids was various with kinds of alkali and acids. The catalyst prepared with pretreatment of HF and HCl in series provided the most Pd fine particles and the best dispersion since it is expected that the last HCl treatment of the active carbon affected to change the surface area for Pd to be dispersed evenly. Crystallinity of Pd was determined by using the same catalyst with XRD. While the catalyst prepared without pretreatment of active carbon was detected with strong Pd peak in XRD pattern due to crystallinity of Pd, the catalyst prepared with pretreatment of two acids was not detected with the peak for Pd. Generally, the crystal size with higher than 50 Å can be detected by XRD. But palladium particle in the prepared catalyst could not be detected by XRD because the particle size is below 50 Å.

Hydrogenolysis of HCFC-142b was performed over the prepared catalysts in Preparation Examples. Catalytic activity test for the hydrogenolysis of HCFC-142b was carried in an apparatus equipped with inconel reactor (Inconel-600) having an outer diameter of ½ inches and a length of 30 cm. Palladium catalyst of 0.5 g (Pd/C) was charged in the reactor and hydrogen gas was passed to reduce the catalyst with a rate of 12 cc/min for 1 hr while increasing the reaction temperature from room temperature to 240° C. Hydrogenolysis of HCFC-142b was performed by supplying $H_2$ and HCFC-142b (molar ratio of $H_2$/HCFC-142b=2–6) at the temperature range of 240–300° C. HF and HCl in the reaction mixture were removed by passing water trap and the trace amount of water was removed with silica gel layer. The obtained reaction mixture was analyzed with gas chromatograph [HP-5890 Series II Plus] connected with FID and poraplot Q capillary column. Further the product was identified with GC/MS[GC: HP-5890, MS Detector: 5971A].

Comparative Example 3

Hydrogenolysis of HCFC-142b Using Pd/AC Catalyst

Hydrogenolysis of HCFC-142b was performed over Pd/AC prepared in Comparative Preparation Example 1 at 270° C. while HCFC-142b and hydrogen gas were supplied with the rate of 2 cc/min and 8 cc/min (molar ratio of H$_2$/HCFC-142b=4), respectively. After 10 hrs, the conversion of HCFC-142b was decreased below 5% and selectivity toward HFC-152a was 58.5%. There were many by-products such as HFC-143a (CH$_3$CF$_3$), ethane, methane and the like.

Comparative Example 4

Hydrogenolysis of HCFC-142b Using Pd/AC—NaOH—HCl Catalyst

Hydrogenolysis of HCFC-142b was performed over Pd/AC—NaOH—HCl catalyst prepared in Comparative Preparation Example 2, according to the procedure of the Comparative Example 3. After the reaction at 270° C. for 50 hrs, the conversion of HCFC-142b was lowered to 42.6% but the selectivity toward HFC-152a was improved to 91.2%. The conversion of HCFC-142b at 240° C. was even lowered to 27.8% and a little improved selectivity of 92.5%.

Comparative Example 5

Hydrogenolysis of HCFC-142b Using Pd/AC—HCl—HF Catalyst

Hydrogenolysis of HCFC-142b was performed over Pd/AC—HCl—HF catalyst prepared in Comparative Preparation Example 3, according to the procedure of the Comparative Example 3. After the reaction at 270° C. for 50 hrs, the conversion of HCFC-142b was 26.2% but the selectivity toward HFC-152a was 93.2%.

EXAMPLE 3

Hydrogenolysis of HCFC-142b using Pd/AC—HF—HCl Catalyst

Hydrogenolysis of HCFC-142b was performed over Pd/AC—HF—HCl catalyst prepared in Preparation Example 1, according to the procedure of the Comparative Example 3. After the reaction at 270° C. for 50 hrs, the conversion of HCFC-142b was improved to 62.7% and the selectivity toward HFC-152a was 93.3%. Even after 10 days of the reaction, the conversion and selectivity were almost not changed. The conversion was improved to 78.5% but the selectivity was lowered a little bit to 91.8% at 300° C. And further, it was proved that the selectivity was improved to 93.2% with additional supply of hydrogen gas (molar ratio of H2/HCFC-142b=5) with the feed rate of 10 cc/min and it was decreased to 84% with lowering the molar ratio to 2.

EXAMPLE 4

Hydrogenolysis of HCFC-142b Using Pd/AC—NaOH—HF—HCl Catalyst

Hydrogenolysis of HCFC-142b was performed over Pd/AC—NaOH—HF—HCl catalyst prepared in Preparation Example 2, according to the procedure of Example 3. After the reaction at 270° C. for 50 hrs, the conversion of HCFC-142b was 63.2% and the selectivity toward HFC-152a was 92.3% and further result was similar to Example 3.

While after hydrogenolysis of HCFC-142b, the Pd peak in Pd/AC catalyst was detected by XRD analysis and it was assigned to palladium and palladium carbide, the other pretreated catalysts did not show the corresponding peaks. That meant that the pretreatment process with alkali or acid not only removed impurities contained therein but also changed the surface characteristics and thus, degree of dispersion was improved and aggregation was also prohibited.

Accordingly, the pretreatment of active carbon with more than two acids highly affected crystalline size and degree of dispersion. And further, this high degree of dispersion maintained effectively the activity of the catalyst.

As a result of intensive studies comparing pretreatment methods, the pretreatment with HF and HCl in series at the end process resulted in the most effective catalyst to convert HCFC-142b to HFC-152a. The activity of the catalyst was excellent at even below 300° C. and optimal reaction conditions such as reaction temperature and molar ratio of reactants were determined. The results were summarized in Table 3.

TABLE 3

Results for Hydrogenolysis of HCFC-142b

| Category | Rate (cc/min) | Temp. (° C.) | Time (h) | Conversion (%) | Selectivity (%) | | | |
|---|---|---|---|---|---|---|---|---|
| | | | | | HFC-152a | HFC-143a | C$_2$H$_6$ | CH$_4$ |
| Com. Exam. 3 | H$_2$ = 8<br>142b = 2 | 270 | 10 | 3.9 | 58.5 | 15.8 | 16.4 | 0.3 |
| Com. Exam. 4 | H$_2$ = 8<br>142b = 2 | 270<br>240 | 50 | 42.6<br>27.8 | 91.2<br>92.5 | 0.8<br>0.6 | 7.8<br>7.2 | 0.2<br>0.2 |
| Com. Exam. 5 | H$_2$ = 8<br>142b = 2 | 270 | 50 | 26.2 | 93.2 | 4.2 | 2.5 | 0.1 |
| Exam. 3 | H$_2$ = 8<br>142b = 2 | 270<br>300 | 50 | 62.7<br>78.5 | 93.3<br>91.8 | 4.9<br>5.4 | 1.7<br>2.6 | 0.1<br>0.2 |
| Exam. 4 | H$_2$ = 8<br>142b = 2 | 270 | 50 | 63.2 | 92.3 | 2.1 | 5.4 | 0.3 |

As summarized in Table 3, the palladium catalyst prepared by pretreatment of two acids (HF and HCl in series) selectively activated the hydrogenolysis of hydrochlorofluorocarbons (HCFCs) to obtain hydrofluorocarbons (HFCs) as substitute materials.

Accordingly, the present invention provides the palladium catalyst prepared by pretreatment of two acids (HF and HCl in series), which shows high conversion at even low temperature and maintains selectivity and activity for long period in the hydrogenolysis of HCFC-142b to HFC-152a and the producing conditions thereof.

What is claimed is:

1. A catalyst for producing 1,1-difluoroethane prepared by impregnating palladium on the pretreated active carbon first with aqueous hydrogen fluoride solution and second with aqueous hydrogen chloride solution in series.

2. A producing method of 1,1-difluoroethane by hydrogenolysis of 1,1-difluoro-1-chloro ethane in the presence of said catalyst of claim 1.

3. The producing method of 1,1-difluoroethane according to claim 1, wherein said catalyst is reduced with hydrogen gas at 200–300° C. before hydrogenolysis.

4. The producing method of 1,1-difluoroethane according to claim 1, wherein said hydrogenolysis is performed at 240–300° C.

5. The producing method of 1,1-difluoroethane according to claim 1, wherein hydrogen and 1,1-difluoro-1-chloro ethane(HFCF-142b) gases are supplied in the ratio of 2–6 ($H_2$/HFCF-142b) in said hydrogenolysis.

* * * * *